United States Patent [19]

Berg et al.

[11] Patent Number: 4,861,436
[45] Date of Patent: Aug. 29, 1989

[54] RECOVERY OF 4-METHYL-2-PENTANONE FROM ACETIC ACID BY DISTILLATION

[75] Inventors: Lloyd Berg, 1314 S. 3rd Ave., Bozeman, Mont. 59715; Richard R. Rall; Marc W. Paffhausen, both of Bozeman, Mont.

[73] Assignee: Lloyd Berg, Bozeman, Mont.

[21] Appl. No.: 307,035

[22] Filed: Feb. 7, 1989

[51] Int. Cl.$^4$ .................. B01D 3/34; C07C 45/82; C07C 45/89
[52] U.S. Cl. .................. 203/38; 203/51; 203/57; 203/61; 203/87; 562/608; 568/302; 568/410
[58] Field of Search .................. 203/38, 39, 87, 51, 203/57, 61; 568/302, 410; 562/608

[56] References Cited

U.S. PATENT DOCUMENTS

| | | | |
|---|---|---|---|
| 2,235,561 | 3/1941 | Nadeau et al. | 568/302 |
| 2,967,888 | 1/1961 | Altenschopfer et al. | 568/302 |
| 3,013,954 | 12/1961 | Pacoud et al. | 203/62 |
| 3,228,985 | 1/1966 | Carpenter et al. | 568/410 |
| 3,480,676 | 11/1969 | Scheuber | 568/302 |
| 4,793,901 | 12/1988 | Berg et al. | 203/61 |

FOREIGN PATENT DOCUMENTS 61-246141  11/1986  Japan .................. 568/302

*Primary Examiner*—Wilbur Bascomb

[57] ABSTRACT

When 4-methyl-2-pentanone and acetic acid mixtures are subjected to extractive distillation with a dimethyl sulfoxide - pelargonic acid mixture as the agent, the acetic acid is converted to gaseous ketene which is easily recovered from the 4-methyl-2-pentanone.

1 Claim, No Drawings

RECOVERY OF 4-METHYL-2-PENTANONE FROM ACETIC ACID BY DISTILLATION

FIELD OF THE INVENTION

This invention relates to a method for recovering 4-methyl-2-pentanone from acetic acid using certain higher boiling liquids as the agent in a rectification column.

DESCRIPTION OF PRIOR ART

Acetic acid and 4-methyl-2-pentanone boil only 2.5 Celcius degrees apart and thus have a relative volatility of only 1.06 Table 1 shows the boiling point relationship for these two compounds at 640 mm. Hg pressure.

TABLE 1

Boiling Points of 4-Methyl-2-pentanone - Acetic Acid Mixtures at 640 mm. Hg.

| % 4-Methyl-2-pentanone | % Acetic Acid | Boiling Point, °C. |
| --- | --- | --- |
| 100 | 0 | 109 |
| 90 | 10 | 110 |
| 77 | 23 | 111 |
| 50 | 50 | 111.2 |
| 40 | 60 | 111.2 |
| 33 | 67 | 111.4 |
| 23 | 77 | 111.4 |
| 10 | 90 | 111.4 |
| 0 | 100 | 111.5 |

From Table 1, it can be seen that in concentrations of 4-methyl-2-pentanone below 77%, the boiling point changes only 0.5° C. and further separation by rectification becomes virtually impossible.

Separation in a rectification column would be possible if an agent could be found which would convert the acetic acid into easy to separate compounds and have no effect on the 4-methyl-2-pentanone.

OBJECTIVE OF THE INVENTION

The object of this invention is to provide a process or method that will make possible the separation of 4-methyl-2-pentanone from acetic acid in a rectification column by adding a higher boiling liquid which at the operating temperature of the column, will convert the acetic acid into useful compounds but have no effect on the 4-methyl-2-pentanone.

SUMMARY OF THE INVENTION

The objects of this invention are provided by a process for separating 4-methyl-2-pentanone from acetic acid which entails the use of dimethylsulfoxide-pelargonic acid mixture as an additive during rectification to convert the acetic acid into ketene and water but not react with the 4-methyl-2-pentanone.

DETAILED DESCRIPTION OF THE INVENTION

We have discovered that when dimethylsulfoxide-pelargonic acid mixtures are added to a rectification column during the distillation of 4-methyl-2-pentanone from acetic acid, the acetic acid will be decomposed exclusively into water and ketene. Ketene has a normal boiling point of −56° C. and comes off overhead in the gaseous phase. The water forms a two-phase azeotrope with the 4-methyl-2-pentanone and comes off in the overhead in the liquid phase. This then forms two liquid layers and can be separated by decantation. The dimethylsulfoxide-pelargonic acid mixture is recovered as bottoms product from the stillpot.

USEFULNESS OF THE INVENTION

The usefulness or utility of this invention can be demonstrated by referring to the data presented in Tables 1 and 2. Table 1 shows that 4-methyl-2-pentanone boils only 2.5° C. lower than acetic acid and is thus extremely difficult to separate by rectification. Table 2 shows that when 4-methyl-2-pentanone-acetic acid mixtures are subjected to dimethylsulfoxide-pelargonic acid mixtures at their normal boiling temperatures in a rectification column, the acetic acid is completely converted to ketene and water. The ketene remains in the gas phase and leaves the condenser. The 4-methyl-2-pentanone and water form two immiscible liquid phases in the condenser and are readily separated by decantation. The dimethylsulfoxide-pelargonic acid mixture is recovered from the stillpot and can be recycled with no further treatment.

WORKING EXAMPLE

1. A glass perforated plate rectification column was calibrated with methylcyclohexane and toluene which possess a relative volatility of 1.46 and found to have 5.3 theoretical plates. A solution consisting of 200 grams comprising 50 wt.% 4-methyl-2-pentanone, 50 wt.% acetic acid was placed in the stillpot and heated. When refluxing began, a mixture comprising 50 wt.% dimethylsulfoxide-50 wt.% pelargonic acid heated to 95° C. was pumped into the column at a rate of 15 ml/min. The heat input to the 4-methyl-2-pentanone-acetic acid in the stillpot was adjusted to give a total reflux rate of 60 ml/min. After a half hour of operation, the overhead and bottoms samples of approximately two ml. were collected and analysed by gas chromatography. The overhead analysis was 37% ketene, 55.6% water, 0.7% acetic acid and 6.7% 4-methyl-2-pentanone and the bottoms analysis was 10% ketene, 11.6% water, 68.4% acetic acid and 10% 4-methyl-2-pentanone. These results are tabulated in Table 2.

| | Time, hr. | Percent Ketene | Percent Water | Percent Acetic acid | Percent 4-Me—2-pentanone |
| --- | --- | --- | --- | --- | --- |
| Overhead | ½ | 37 | 55.6 | 0.7 | 6.7 |
| Bottoms | | 10 | 11.6 | 68.4 | 10 |

The ketene boils at −56° C. and vaporizes off the overhead leaving a two layer immiscible liquid. Decantation of the aqueous layer yields the high purity 4-methyl-2-pentanone. Collecting the ketene vapor yields this compound in high purity as well. At present, ketene is the most valuable product obtained in this process.

We claim:

1. A method for recovering 4-methyl-2-pentanone from mixtures of 4-methyl-2-pentanone and acetic acid which comprises contacting a mixture of 4-methyl-2-pentanone and acetic acid with a mixture of dimethylsulfoxide and pelargonic acid in a rectification column, heating said mixtures in said column, allowing the acetic acid to decompose into ketene and water while in the rectification column, recovering the ketene, 4-methyl-2-pentanone and water as an overhead vapor stream, partially condensing the overhead vapor stream to recover ketene as a gaseous stream and 4-methyl-2-pentanone and water as a condensed liquid stream, separating the gaseous ketene stream from the condensed liquid stream, separating the condensed liquid stream into a 4-methyl-2-pentanone phase and a water phase, separating the two phases by decantation and obtaining the dimethylsulfoxide-pelargonic acid mixture and any undecomposed acetic acid from the stillpot.

* * * * *